Figure 1:
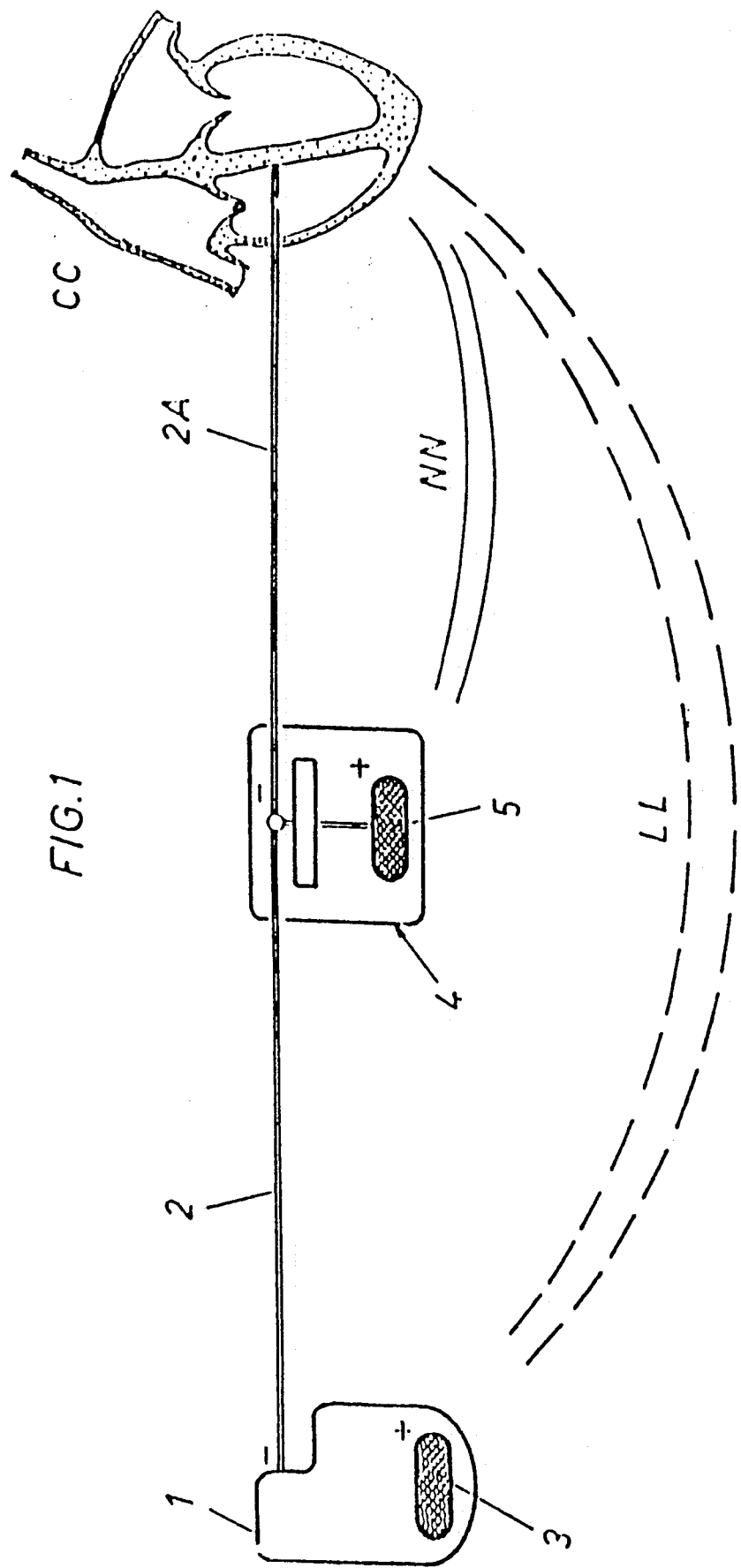

United States Patent [19]

De Bellis

[11] Patent Number: 5,012,806

[45] Date of Patent: May 7, 1991

[54] IMPLANTATIONS FOR CARDIAC STIMULATION BY PACEMAKER

[76] Inventor: Ferruccio De Bellis, Viale Pola,23, 00198 Rome, Italy

[21] Appl. No.: 243,782

[22] PCT Filed: Nov. 11, 1987

[86] PCT No.: PCT/IT87/00096

§ 371 Date: Jul. 8, 1988

§ 102(e) Date: Jul. 8, 1988

[87] PCT Pub. No.: WO88/03423

PCT Pub. Date: May 19, 1988

[30] Foreign Application Priority Data

Nov. 11, 1986 [IT] Italy .............................. 48642 A/86

[51] Int. Cl.[5] ................................................. A61N 1/00
[52] U.S. Cl. ................................. 128/419 P; 128/903; 128/419 PG
[58] Field of Search ............... 128/419 PG, 419 P, 903

[56] References Cited

U.S. PATENT DOCUMENTS

| 3,977,411 | 8/1976 | Hughes, Jr. et al. | 128/419 P |
| 4,402,322 | 9/1983 | Duggan | 128/419 PG |
| 4,424,812 | 1/1984 | Lesnick | 128/419 PG |
| 4,590,944 | 5/1986 | Mann et al. | 128/419 PG |

FOREIGN PATENT DOCUMENTS

| 86-05698 | 9/1986 | PCT Int'l Appl. | 128/419 PG |
| 2053688 | 7/1979 | United Kingdom | 128/419 PG |

Primary Examiner—Francis Jaworski
Assistant Examiner—George Manuel

[57] ABSTRACT

Implantation for cardiac stimulation by pacemaker including also a radio-frequency receiver for alternative cardiac stimulation by means of an external pacemaker and a radio-frequency transmitter; wherein the radio-frequency receiver is not equipped with the usual plate in contact with the patient's tissues and is clamped on a bipolar electrode connecting the pacemaker to the heart. In this way, the stimulating signals either from the pacemaker or, in alternative, from the external transmitter, are transmitted through this electrode, being the pacemaker also insulated and without the external plate in contact with the patient's tissue. As a modification wherein the pacemaker is equipped with the plate in contact with the patient's tissue, the electrode length connecting the pacemaker with the radio-frequency receiver is unipolar while the length of electrode connecting the radio-frequency receiver to the heart remains bipolar.

5 Claims, 2 Drawing Sheets

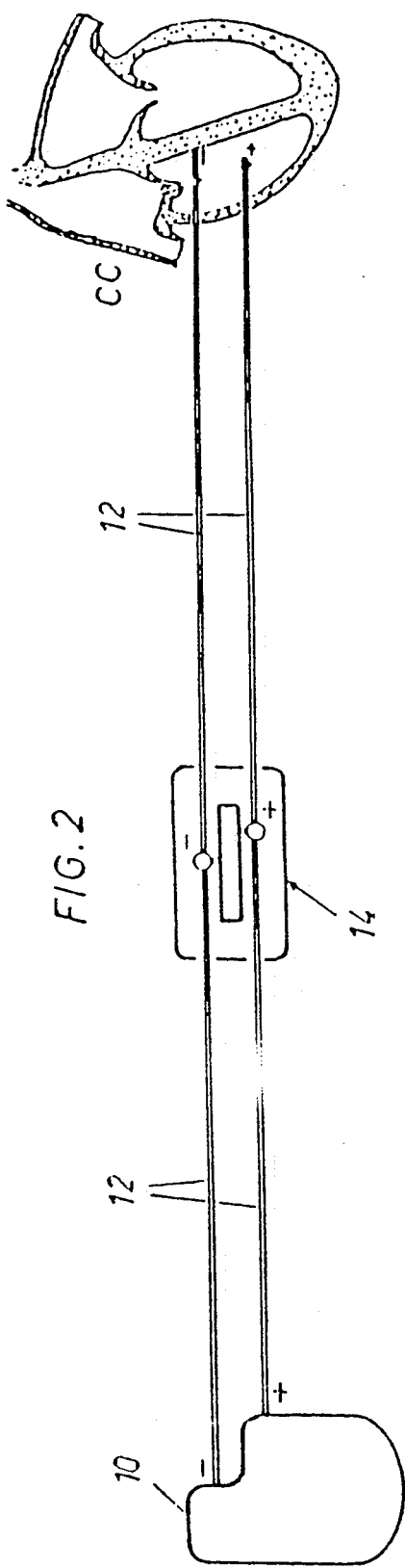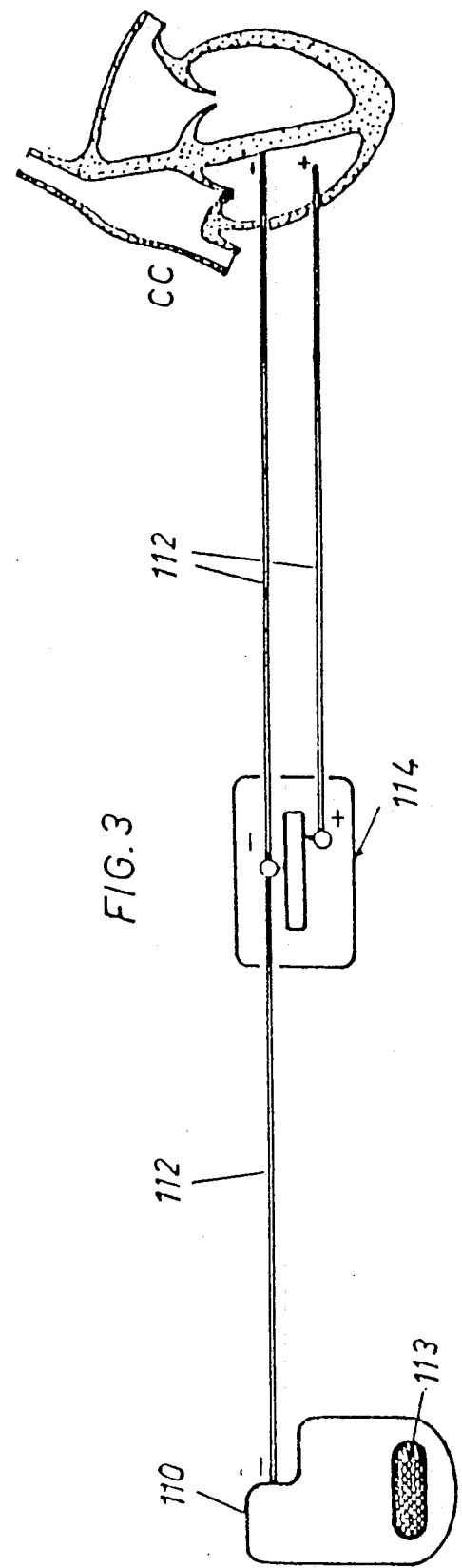
FIG. 2
FIG. 3

IMPLANTATIONS FOR CARDIAC STIMULATION BY PACEMAKER

This invention relates to artificial cardiac stimulation and more precisely to implantations for cardiac stimulation equipped with a radio-frequency receiver suitable to receive stimulating signals, alternative to those from the pacemaker, transmitted by a radio-frequency transmitter external to the patient, if necessary.

Usually, in these implantations, the electrode connecting the pacemaker to the heart is unipolar and a radio-frequency receiver is inserted thereon having a plate on the outside of its casing that is in contact with the patient's tissues.

The pacemaker too has a plate in contact with the patient's tissue and in case of stimulation both from the implanted pacemaker and alternatively from the external transmitter, one of the polarities of the stimulating signals (normally the negative) is transmitted through the electrode while the other polarity (the positive) is closed from the heart onto the contact plates through the tissue of the patient.

This present arrangement has some drawbacks both as regards the pacemaker operation and implant structure, particularly the radio-frequency receiver structure.

The drawback in the operation of the present stimulation implants is the high density of the current transmitted through the patient tissue that may induce undesirable muscular contractions in the patient's thorax.

The structural drawback is the size of the contact plate of the radio-frequency receiver that cannot be reduced beyond a certain point, therefore limiting the miniaturization of the receiving coil.

Accordingly is an object of the invention to provide an improved stimulating implantation of the type in question wherein the afore mentioned drawbacks are overcome by making use of a continuous bipolar electrode whereon a radio-frequency receiver is clamped deprived of the contact plate usually equipping the radio receivers now in use.

This continuous bipolar electrode connects the permanently implanted pacemaker to the patient's heart.

Nevertheless, the electrode of the invention can be utilized also in the case where the implanted pacemaker has the contact plate and such a plate can be utilized by connecting the pacemaker and the radio-frequency receiver by an unipolar length of electrode, provided that the plate-less receiver is still connected to the heart by a length of bipolar electrode.

The invention is described in details with reference to the attached schematic drawings, wherein:

FIG. 1 schematically shows a cardiac stimulation implantation of the type presently in use;

FIG. 2 is a similar view of the implantation according to the invention where use is made of a radio-frequency receiver and pacemaker deprived of the external contact plate; and FIG. 3 is a similar view of a second embodiment of the invention, wherein only the radio-frequency receiver is deprived of the contact plate while such a plate equips the pacemaker, and the electrode length comprised between the pacemaker and radioreceiver is accordingly unipolar.

As known, cardiac stimulation implantations equipped with a receiving device for alternative stimulation to that of the implanted pacemaker, have presently a large diffusion.

These implantations allow a cardiac stimulation alternative to that provided by the implanted pacemaker, by utilizing an external pacemaker and transmitter capable of transmitting stimulation signals on a precise radio-frequency whereon also the receiver is tuned. The receiver is clamped on the continuous electrode that connects the pacemaker to the heart and has a plate for the electric contact with the patient's tissue.

The stimulating signals picked up by the radio-frequency receiver are sent to the heart through the electrode, the positive polarity being closed through the patient's tissue onto the radio-frequency receiver contact plate.

Normally in this type of implantation the pacemaker too has a plate in contact with the patient's tissue and during normal operation the negative polarity of stimulating signals is sent by the pacemaker to the heart through the unique conductor of the unipolar electrode, while the positive polarity is closed through the patient's tissue onto the pacemaker contact plate.

This mode of operation is schematically shown in FIG. 1 that illustrates a traditional implantation for cardiac stimulation equipped with a radio-frequency receiver for alternative stimulation wherein the negative polarity of the signals generated by pacemaker 1 is sent to the patient's heart CC through electrode 2 while the positive polarity closes from the heart onto the contact plate 3 through the patient's tissue. This condition of normal operation is shown in FIG. 1 by the dotted lines LL.

Also in case of alternative cardiac stimulation provided by signals generated by an external pacemaker (not shown) and transmitted through radio-frequency waves to the receiver 4, the picked-up signals (negative polarity) are sent to the heart CC through unipolar electrode 2A connecting the heart to the receiver 4, while the positive plarity closes from the heart onto external plate 5 of receiver 4 through the patient's tissue.

This condition is shown in FIG. 1 by the continuous lines NN. In other words, in these implantations, both in normal stimulation mode and during alternative stimulation from outside by radio-frequency signals, the patient's tissues are utilized as earth return; as mentioned this represents a drawback because there is the possibility of passage of high density currents through said tissues that may cause bothersome and undesirable muscular contractions.

Moreover the necessity of utilizing a contact plate 5 of suitable dimensions prevents the reduction of the size of the receiver.

These drawbacks are completely overcome by the improvement of the invention according to which the external contact plates of both the pacemaker and radio-frequency receiver are eliminated.

This condition is represented in FIG. 2 wherein the pacemaker 10 is no longer equipped with the external plate in contact with the patient's tissue and is connected to heart CC through a bipolar electrode 12.

Also the radio-frequency receiver 14 is deprived of the external plate in contact with the patient's tissue and its two outputs for the two polarities of the alternative stimulation signals are connected to the two conductors of bipolar electrode 12 whereupon receiver 14 is clamped.

In both cases of normal and alternative stimulation the two polarities of the stimulating signals are transmitted to heart CC each through a separate conductor, thus eliminating the necessity of transmitting high-density current pulses through the patient's tissue.

FIG. 3 illustrates a modification of the invention wherein the radio-frequency receiver has no contact plate while the pacemaker is still equipped with such a plate in contact with the patient's tissue.

In this embodiment of the invention, pacemaker 110 is of a type normally available on the market and its external plate 113 is in contact with the patient's tissue.

Accordingly therein, the length of electrode 112 between pacemaker 110 and radio-frequency receiver 114 is unipolar, while the length of electrode 112A between the radioreceiver and the heart is bipolar.

During normal operation of pacemaker 110 the negative polarity of the stimulating signals is transmitted to heart CC through one of the conductors of bipolar electrode 112A while the positive polarity will close onto plate 113 through the patient's tissue.

Nothing changes, in respect to the embodiment of FIG. 2, in case of alternative stimulation by the external radio-frequency pacemaker; in fact also in this embodiment the polarities o the stimulating signals picked up by the radioreceiver will be transmitted to the patient's heart through the bipolar length of electrode 112A.

I claim:

1. A cardiac stimulation implantation through a pacemaker adapted for implantation within a patient's body including an electrode adapted to be connected to the patient's heart, equipped with a radio-frequency receiver for alternative stimulation by a pacemaker located external to the patient's body and a radio-frequency transmitter, wherein the radio-frequency receiver is clamped on said electrode, characterized in that said electrode is a two-lead bipolar electrode at least in the length between said radio receiver and the patient's heart, and the outgoing and return current paths for stimulating signals produced by the radio-frequency receiver are through the bipolar electrode, and not through the patient's tissue, such that the radio-frequency receiver requires no contact plate for connection to the patient's tissue.

2. The cardiac stimulation implantation of claim 1 wherein said electrode is a two-lead bipolar electrode along its whole length from the internal pacemaker to the heart, and the outgoing and return current paths for stimulating signals produced by the internal pacemaker are through the bipolar electrode and not through the patient's tissue, such that the internal pacemaker requires no contact plate for connecting to the patient's tissue.

3. A cardiac stimulation device adapted for implantation within a patient's body comprising:
   a pacemaker for the generation of heart stimulation pulses;
   a radio frequency receiver responsive to radio frequency signal for producing alternative heart stimulation pulses in the event of a failure of the pacemaker; and
   an electrode adapted for connection between the pacemaker, the radio frequency receiver and the patient's heart which is bipolar along its length between at least the radio frequency receiver and the patient's heart such that the outgoing and return current paths for the alternative heart stimulation pulses are through the bipolar electrode and not through the patient's tissue and the radio frequency receiver requires no contact plate for connection to the patient's tissue.

4. A cardiac stimulation device according to claim 3 wherein the bipolar electrode is continuous along its entire length between the heart, the radio frequency receiver and the pacemaker.

5. A cardiac stimulation device adapted for implantation within a patient's body comprising:
   a pacemaker for the generation of heart stimulation pulses;
   a radio frequency receiver responsive to radio frequency signals for producing alternative heart stimulation pulses in the vent of a failure of the pacemaker; and
   an electrode adapted for connection between the pacemaker, the radio frequency receiver and the patient's heart which is bipolar along its length between the pacemaker and the patient's heart such that the outgoing and return current paths for the heart stimulation pulses produced by the pacemaker are through the bipolar electrode and not through the patient's tissue, and the pacemaker requires no contact plate for connection to the patient's tissue.

* * * * *

UNITED STATES PATENT AND TRADEMARK OFFICE
CERTIFICATE OF CORRECTION

PATENT NO. : 5,012,806

DATED : May 7, 1991

INVENTOR(S) : DeBellis, Ferruccio

It is certified that error appears in the above-identified patent and that said Letters Patent is hereby corrected as shown below:

In claim 3, column 4, line 12, "signal" should be -- signals --.

In claim 5, column 4, line 35, "in the vent" should be -- in the event --.

Signed and Sealed this

Fifteenth Day of September, 1992

Attest:

DOUGLAS B. COMER

*Attesting Officer*  *Acting Commissioner of Patents and Trademarks*